United States Patent [19]
Moon et al.

[11] Patent Number: 5,639,878
[45] Date of Patent: Jun. 17, 1997

[54] ACYLOXYLATION PROCESS FOR PREPARING 4-ACYLOXY-2-AZETIDINONE DERIVATIVES

[75] Inventors: Chi Jang Moon, Kyunggi-do; Kyung Up Baik, Daejeon; Sea Han Oh, Seoul; Joon Wan Kim; Jae Ho Lee, both of Kyunggi-do, all of Rep. of Korea

[73] Assignee: Daewoong Pharmaceutical Co., Ltd., Kyunggi-do, Rep. of Korea

[21] Appl. No.: 506,052

[22] Filed: Jul. 24, 1995

[30] Foreign Application Priority Data

Jul. 29, 1994 [KR] Rep. of Korea ...................... 94-18725

[51] Int. Cl.$^6$ .......................... C07D 205/08; C07B 41/12
[52] U.S. Cl. .......................................................... 540/357
[58] Field of Search .............................................. 540/357

[56] References Cited

FOREIGN PATENT DOCUMENTS

| 0167155 | 1/1986 | European Pat. Off. . |
| 0372699 | 8/1990 | European Pat. Off. . |
| 0488611A1 | 6/1992 | European Pat. Off. . |
| 59-44355 | 3/1984 | Japan . |
| 61-97260 | 5/1986 | Japan . |
| 62-84057 | 4/1987 | Japan . |

OTHER PUBLICATIONS

Brain, J.C.S. Chem Comm 1972, p. 229.
Tetrahedron Letters, vol. 22, No. 51, pp. 5205–5208, 1981 (Shiozaki et al.).
Tetrahedron Letters, vol. 30, No. 41, pp. 5631–5634, 1989 (Ito).
Tetrahedron Letters, vol. 23, No. 22, pp. 2293–2296, 1982 (Neider).
J. Am. Chem. Soc. 1990, 112, pp. 7820–7822 Murahashi.
Chem. Pharm, Bull. 29(10) 2899–2909 (1981) (Yoshida et al.).

*Primary Examiner*—Mark L. Berch
*Attorney, Agent, or Firm*—Lowe, Price, LeBlanc & Becker

[57] ABSTRACT

The present invention relates to a novel and improved process for preparing 4-acyloxy-2-azetidinone derivatives having the following formula (I) which are useful as an intermediate for synthesis of penem or carbapenem compounds:

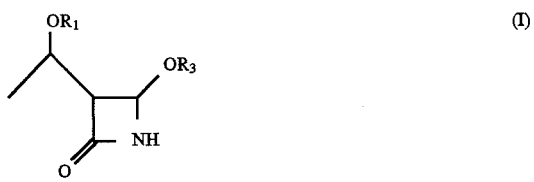

in which $R_1$ represents a hydroxy-protecting group; and $R_3$ represents an acyl group, which comprises reacting an azetidinone derivative having the following formula (II):

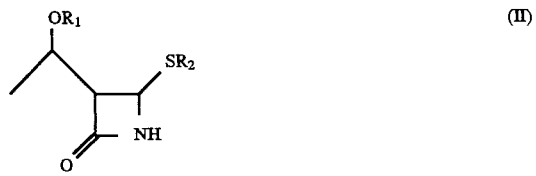

wherein $R_1$ is defined as above and $R_2$ represents an alkyl group or an aryl group, with a N-haloacylimide in the presence of an organic carboxylic acid or a salt of an organic carboxylic acid.

The present invention uses the organic compound, N-haloacylimide, as the reactant rather than the heavy metal reactant used in the prior art, and thus provides an economical advantage and does not cause any problem related to safety and waste disposal after the reaction.

13 Claims, No Drawings

ACYLOXYLATION PROCESS FOR PREPARING 4-ACYLOXY-2-AZETIDINONE DERIVATIVES

BACKGROUND OF THE INVENTION

1. Field of the Invention

The present invention relates to a novel and improved process for preparing 4-acyloxy-2-azetidinone derivatives which is an intermediate useful for synthesis of penem or carbapenem antibiotics. More specifically, the present invention relates to a novel process for preparing 4-acyloxy-2-azetidinone derivatives having the following formula (I):

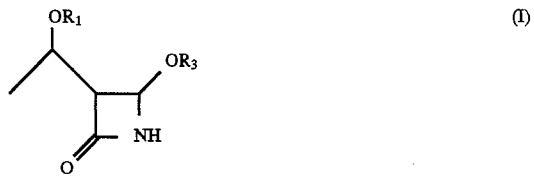

or their optical isomers, in which $R_1$ represents a hydroxy-protecting group; and
$R_3$ represents an acyl group.

2. Background Art

3-[1'-(R)-hydroxyethyl]-4-acyloxy-2-azetidinone, and its derivatives in which hydroxy group or β-lactam amino group is protected with various protecting groups have been used as an intermediate for synthesis of penem compounds or carbapenem compounds, and the methods for their preparation have been disclosed in numerous publications. Typical examples of the known methods are a method for preparing 4-acetoxy-2-azetidinone derivatives from 4-acetyl-2-azetidinone derivatives by means of Baeyer-Villiger oxidation [see, Tetrahedron Lett., 5205 (1981); 5631 (1989)]; a method for preparing 4-acetoxy-2-azetidinone derivatives from 4-hydroxycarbonyl-2-azetidinone derivatives using Pb(OAc)4 [see, Tetrahedron Lett., 2923 (1982)]; a method for preparing 4-acetoxy-2-azetidinone from 4-trialkylsilyloxy-2-azetidinone derivatives [see, Japanese Laid-open Patent Publication No. 84057/87; European Patent No. 167155]; a method for preparing 4-acetoxy-2-azetidinone derivatives from 2-azetidinone derivatives having no substituent on C-4 position [see, European Patent No. 488611; J. Am. Chem. Soc., 7820 (1990)], and the like.

In addition, some methods for preparing 3-[1'-(R)-hydroxyethyl]-4-arylthio-2-azetidinone derivatives, for example, a method for preparing 4-arylthio-2-azetidinone derivatives by condensation reaction of isocyanate derivatives and vinyl sulfide derivatives [see, Japanese Laid-open Patent Publication No. 97260/86], a method for preparing 3-(1-hydroxyethyl)-4-arylthio-2-azetidinone derivatives by introducing 1-hydroxyethyl group into C-3 position of 4-arylthio-2-azetidinone derivatives in which C-3 position remains unsubstituted [see, Japanese Laid-open Patent Publication No. 44355/84] and the like, have also been reported. Said arylthio derivatives are generally converted into the 4-acyloxy or 4-arylsulfone derivatives which are used for preparing 3-[1'-(R)-hydroxyethyl]-4-acyloxy-2-azetidinone derivatives. Particularly, the arylthio compounds have mainly converted into 4-acyloxy-2-azetidinone derivatives because of high reactivity of the compound having 4-acyloxy group.

Accordingly, the method for conversion of azetidinone derivatives having 4-arylthio group into 4-acyloxy compounds have been extensively studied. The presently known methods are a method using mercury salt [see, Chem. Pharm. Bull., 2899 (1981)] or copper salt [see, European Patent No. 372699].

However, the method using mercury salt could not be practically used in industrial scale because the use of a poisonous mercury salt as the reactant results in serious problems related to safety in operations and disposal of mercury-containing waste after the reaction. The method using copper salt has been proposed as an alternative method for such impractical method. However, although the copper salt is less poisonous than mercury salt, since copper itself is a heavy metal, the problem related to disposal of reaction waste could not be completely solved. Moreover, such heavy metal reactants are expensive and thus are not preferable in economical view.

Thus, the present inventors have extensively and intensively studied to develop a method which can convert 4-arylthio azetidinone compounds into 4-acyloxy azetidinone derivatives with a certain reactant, which is economical and can be safely handled, rather than heavy metal reactants used in the prior methods. As a result, we have identified that 3-[1'-(R)-hydroxyethyl]-4-arylthio-2-azetidinone can be economically and safely converted into 3-[1'-(R)-hydroxyethyl]-4-acyloxy-2-azetidinone by means of an organic compound, N-haloacylimide, as the reactant, which does not cause any problem related to toxicity and waste disposal. Thus, now we have completed the present invention.

Therefore, it is an object of the present invention to provide a novel process for preparing 4-acyloxy-2-azetidinone derivatives of formula (I), as defined above, using a N-haloacylimide reactant.

It is a further object of the present invention to provide a novel and improved process for preparing 4-acyloxy-2-azetidinone derivatives of formula (I), as defined above, or their optical isomers by reacting an 2-azetidinone derivative of formula (II), as defined below, with a N-haloacylimide in the presence of an organic carboxylic acid or a salt of an organic carboxylic acid.

The foregoing has outlined some of the more pertinent objects of the present invention. These objects should be construed to be merely illustrative of some of the more pertinent features and applications of the invention. Other many beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

According to the present invention, a novel and improved process for preparing 4-acyloxy-2-azetidinone derivatives having the following formula (I):

or their optical isomers in which $R_1$ represents a hydroxy-protecting group; and
$R_3$ represents an acyl group, which comprises reacting an 2-azetidinone derivative having the following formula (II):

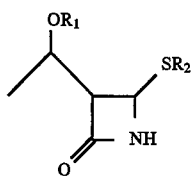

wherein $R_1$ is defined as above and $R_2$ represents an alkyl group or an aryl group, with a N-haloacylimide in the presence of an organic carboxylic acid or a salt of an organic carboxylic acid.

In the definitions of substituents for the above formulae, the hydroxy-protecting group for $R_1$ can be any hydroxy-protecting group conventionally used in this technical field and include, for example, acyl groups such as carbamoyl, aliphatic acyl, aromatic acyl, heterocyclic acyl, and aliphatic acyl substituted with aromatic group(s) or heterocyclic group(s) derived from carboxylic acids, carbonic acids, sulfonic acids and carbamic acids; ar(lower)alkyl groups such as mono- or di- or tri-phenyl(lower)alkyl (e.g. benzyl, benzhydryl, trityl, etc.); tri-substituted silyl groups such as tri(lower)alkylsilyl (e.g. trimethylsilyl, triethylsilyl, isopropyldimethylsilyl, t-butyl-dimethylsilyl, diisopropylmethylsilyl, dimethylhexylsilyl, etc.), triarylsilyl (e.g. triphenylsilyl, etc.), triar(lower)alkylsilyl (e.g. tribenzylsilyl, etc.), etc., and the like. Preferred hydroxy-protecting group may be t-butyldimethylsilyl, triethylsilyl, dimethylhexylsilyl, p-nitrobenzyloxycarbonyl, p-methoxybenzyloxycarbonyl, allyloxycarbonyl, and the like. Particularly preferred hydroxy-protecting group $R_1$ is t-butyldimethylsilyl group.

The alkyl or aryl group for substituent $R_2$ present in the formula (II) is a group which is eliminated together with the adjacent sulfur(S) atom during the reaction and thus can be any alkyl or aryl group which does not adversely affect the reaction according to the present invention. Preferred $R_2$ group may be lower alkyl groups having 1 to 4 carbon atoms such as methyl, ethyl, propyl or butyl, or phenyl, alkylphenyl or alkoxyphenyl groups having 1 to 4 carbon atoms in alkyl or alkoxy moiety, halophenyl groups, and the like.

The acyl group for substituent $R_3$ is derived from the organic carboxylic acid or the salt of organic carboxylic acid present in the reaction mixture. Preferred example of the acyl group includes formyl, acetyl, chloroacetyl, trichloroacetyl, fluoroacetyl, trifluoroacetyl, propionyl, butyryl, isobutyryl, valeryl, pivaloyl, benzoyl, halobenzoyl, methoxybenzoyl and the like groups. Particularly preferred acyl group for $R_3$ is acetyl or benzoyl.

Typical example of N-haloacylimide used as the reactant in the process according to the present invention can include N-bromosuccinimide, N-bromophthalimide, N-chlorosuccinimide, N-chlorophthalimide, N-iodosuccinimide, N-iodophthalimide, and the like.

As the source for acyl group in the process of the present invention, an organic carboxylic acid or a salt of organic carboxylic acid can be used. Specific examples of such organic carboxylic acid or its salt include aliphatic carboxylic acids such as acetic acid, chloroacetic acid, trichloroacetic acid, fluoroacetic acid, trifluoroacetic acid, propionic acid, butyric acid, isobutyric acid, valetic acid, etc., aromatic carboxylic acids such as substituted or unsubstituted benzoic acid, or metal salts of carboxylic acids such as sodium or potassium salt of said carboxylic acids, and ammonium carboxylate, and the like.

According to the process of the present invention, the desired 4-acyloxy-2-azetidinone derivative of formula (I) can be conveniently prepared by reacting 4-aryl(or alkyl) thio-2-azetidinone derivative of formula (II) with N-haloacylimide in the presence of the organic carboxylic acid or its salt such as aromatic or aliphatic carboxylic acid as the source of acyl group. If necessary, the optical isomer of 4-acyloxy-2-azetidinone derivative of formula (I) can be directly prepared starting from the corresponding optical isomer of 4-aryl(or alkyl)thio-2-azetidinone derivative of formula (II).

The reaction according to the process of the present invention can be preferably carried out in the presence of a solvent. As the solvent suitable for this purpose, any solvent which does not adversely affect the reaction can be used. Preferably, a reaction-inert organic solvent such as, for example, dichloromethane, chloroform, tetrahydrofuran, acetonitrile, dimethylformamide, benzene, etc. can be used.

The reaction according to the present invention is preferably carried out under atmosphere, although it can be conducted under inert atmosphere, for example, argon or nitrogen gas. The reaction temperature carrying out the reaction of the present invention can be varied depending on the kind of N-haloacylimide and reaction solvent used in the reaction and is generally in the range of −50° C. to boiling point of the solvent used therein, preferably in the range of −20° C. to room temperature. The reaction time is generally 10 minutes to 24 hours, preferably 10 minutes to 5 hours.

In the reaction according to the present invention, N-haloacylimide is generally used in the ratio 1 to 2 equivalent weights, preferably 1 to 1.2 equivalent weights, with respect to one equivalent weight of the compound of formula (II); and the organic carboxylic acid or its salt as the source of acyl group is used in the ratio of 1 to 5 equivalent weights, preferably 1 to 2 equivalent weights, with respect to one equivalent weight of the compound of formula (II).

When the reaction is completed, the reaction mixture can be conveniently subjected to conventional working-up procedure to isolate the desired 4-acyloxy-2-azetidinone derivative of formula (I). For example, after the reaction is completed, the reaction mixture is diluted with an organic solvent such as ethyl ether, ethyl acetate, dichloromethane, etc., and then washed with an aqueous alkaline solution such as aqueous sodium bicarbonate solution- The organic layer is concentrated and then the residue is treated with a non-polar solvent such as n-hexane to crystallize the desired compound of formula (I). If required, the resulting desired compound of formula (I) in a crystallized form may be further purified by means of a conventional method such as column chromatography, fractional thin layer chromatography, recrystallization, and the like.

The present invention will be more specifically explained on the basis of the following examples. However, it should be understood that the present invention is not limited by these examples in any manner.

EXAMPLE 1

Synthesis of (1'R, 3R, 4R)-3-(1'-t-butyldimethylsilyloxy)ethyl-4-acetoxy-2-azetidinone 337 mg (1 mmole) of (1'R, 3S, 4R)-3-(1'-t-butyldimethylsilyloxy)ethyl-4-phenylthio-2-azetidinone and 0.23 ml (2 mmole) of acetic acid were dissolved in 10 ml of dichloromethane and 147 mg (1.1 mmole) of N-chlorosuccinimide was added thereto. The reaction solution was stirred for 5 hours at room temperature and then aqueous solution of sodium thiosulfate was added thereto. The organic layer was separated, washed successively with water, aqueous sodium bicarbonate solution and saline, dried over anhydrous sodium sulfate and then filtered. The filtrate was concentrated under reduced pressure. The residue was subjected to column chromatography eluting with ethyl acetate/n-hexane(7:3) to obtain 274 mg (Yield 95.3%) of the title compound as a white crystal.

TLC: Rf 0.5 (ethyl acetate:n-hexane=7:3)

$[\alpha]_{26}$: +51.7 (c=0.226, CHCl$_3$)

$^1$H-NMR (CDCl$_3$, δppm): 0.06(6H, d), 0.85(9H, s), 1.25 (3H, d), 2.1(3H, s), 3.2(1H, dd), 4.2(1H, 5.8(1H, d), 6.4(1H, bs)

EXAMPLE 2

Synthesis of (1'R, 3R, 4R)-3-(1'-t-butyldimethylsilyloxy)ethyl-4-acetoxy-2-azetidinone 675 mg (2 mmole) of (1'R, 3S, 4R)-3-(1'-t-butyldimethylsilyl-oxy)ethyl-4-phenylthio-2-azetidinone and 0.46 ml (4 mmole) of acetic acid were dissolved in 20 ml of dichloromethane and 392 mg (2.2 mmole) of N-bromosuccinimide was added thereto. The reaction solution was then stirred for 10 minutes at 0° C. The reaction mixture was treated according to the same procedure as Example 1 to obtain 542 mg (Yield 94.3%) of the title compound as a white crystal.

EXAMPLE 3

Synthesis of 1'R, 3R, 4R)-3-(1'-t-butyldimethylsilyloxy)ethyl-4-acetoxy-2-azetidinone 337 mg (1 mmole) of (1'R, 3S, 4R)-3-(1'-t-butyldimethylsilyloxy)ethyl-4-phenylthio-2-azetidinone and 0.23 ml (2 mmole) of acetic acid were dissolved in 10 ml of dichloromethane and 247 mg (1.1 mmole) of N-iodosuccinimide was added thereto at −20° C. The reaction solution was then stirred for 10 minutes. The reaction mixture was treated according to the same procedure as Example 1 to obtain 249 mg (Yield 86.6%) of the title compound as a white crystal.

EXAMPLE 4

Synthesis of (1'R, 3R, 4R)-3-(1'-t-butyldimethylsilyloxy)ethyl -4-acetoxy-2-azetidinone 337 mg (1 mmole) of (1'R, 3S, 4R)-3-(1'-t-butyldimethylsilyloxy)ethyl-4-phenylthio-2-azetidinone and 196 mg (2 mmole) of potassium acetate were dissolved in 10 ml of N,N-dimethylformamide and 196 mg (1.1 mmole) of N-bromosuccinimide was added thereto at 0° C. The reaction solution was then stirred for 10 minutes. The reaction mixture was treated according to the same procedure as Example 1 to obtain 243 mg (Yield 84.5%) of the title compound as a white crystal.

EXAMPLE 5

Synthesis of (1'R, 3R, 4R)-3-(1'-t-butyldimethylsilyloxy)ethyl-4-benzoyloxy-2-azetidinone 337 mg (1 mmole) of (1'R, 3S, 4R)-3-(1'-t-butyldimethylsilyloxy)ethyl-4-phenylthio-2-azetidinone and 244 mg (2 mmole) of benzoic acid were dissolved in 10 ml of dichloromethane and 196 mg (1.1 mmole) of N-bromosuccinimide was added thereto at 0° C. The reaction solution was then stirred for 10 minutes. The reaction mixture was treated according to the same procedure as Example 1 to obtain 150 mg (Yield 52.2%) of the title compound as a white crystal.

$^1$H-NMR (CDCl$_3$, δppm): 0.06(6H, d), 0.85(9H, s), 1.3 (3H, d), 3.36(3H, dd), 4.28(1H, m), 6.1(1H, d), 6.7(1H, bs), 7.46(2H, t), 7.6(1H, t), 8.04(1H, d)

EXAMPLE 6

Synthesis of (1'R, 3R, 4R)-3-(1'-t-butyldimethylsilyloxy)ethyl-4-acetoxy-2-azetidinone 295 mg (1 mmole) of (1'R, 3S, 4R)-3-(1'-t-butyldimethylsilyloxy)ethyl-4-methylthio-2-azetidinone and 0.23 ml (2 mmole) of acetic acid were dissolved in 10 ml of dichloromethane and 196 mg (1.1 mmole) of N-bromosuccinimide was added thereto at 0° C. The reaction solution was then stirred for 10 minutes. The reaction mixture was treated according to the same procedure as Example 1 to obtain 234 mg (Yield 81.4%) of the title compound as a white crystal.

EXAMPLE 7

Synthesis of (1'R, 3R, 4R)-3-(1'-t-butyldimethylsilyloxy)ethyl-4-acetoxy-2-azetidinone 367 mg (1 mmole) of (1'R, 3S, 4R)-3-(1'-t-butyldimethylsilyloxy)ethyl-4-o-methoxyphenylthio-2-azetidinone and 0.23 ml (2 mmole) of acetic acid were dissolved in 10 ml of dichloromethane and 196 mg (1.1 mmole) of N-bromosuccinimide was added thereto at 0° C. The reaction solution was then stirred for 10 minutes. The reaction mixture was treated according to the same procedure as Example 1 to obtain 250 mg (Yield 87%) of the title compound as a white crystal.

EXAMPLE 8

Synthesis of (1'R, 3R, 4R)-3-(1'-t-butyldimethylsilyloxy)ethyl-4-acetoxy-2-azetidinone 337 mg (1 mmole) of (1'R, 3S, 4R)-3-(1'-t-butyldimethylsilyloxy)ethyl-4-phenylthio-2-azetidinone and 0.23 ml (2 mmole) of acetic acid were dissolved in 10 ml of dichloromethane and 251 mg (1.1 mmole) of N-bromophthalimide was added thereto at 0° C. The reaction solution was then stirred for 10 minutes. The reaction mixture was treated according to the same procedure as Example 1 to obtain 265 mg (Yield 92.2%) of the title compound as a white crystal.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A process for preparing 4-acyloxy-2-azetidinone derivatives having the following formula (I):

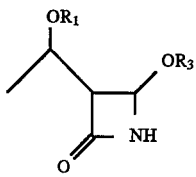

(I)

or their optical isomers, in which

R₁ represents a hydroxy-protecting group; and
R₃ represents a group selected from the group consisting of formyl, acetyl, chloroacetyl, trichloroacetyl, fluoroacetyl, trifluoroacetyl, propionyl, butyryl, isobutyrl, valeryl, pivaloyl, benzoyl, halobenzoyl and methoxybenzoyl, which comprises reacting an azetidinone derivative having the following formula (II):

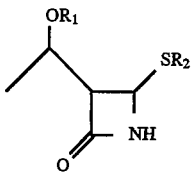

(II)

wherein R₁ is defined as above and R₂ represents an alkyl group or an aryl group, with a N-haloacylimide selected from the group consisting of N-chlorosuccinimide, N-bromophthalimide, N-chlorophthalimide, N-iodosuccinimide and N-iodophthalimide, in the presence of an organic carboxylic acid or a salt of an organic carboxylic acid.

2. The process according to claim 1, wherein an optical isomer of the azetidinone derivative of formula (II) is used as the starting material to obtain the optical isomer of 4-acyloxy-2-azetidinone derivative of formula (I).

3. The process according to claim 1, wherein R₁ represents t-butyldimethylsilyl group, R₂ represents alkyl group having 1 to 4 carbon atoms, or phenyl group substituted or unsubstituted with alkyl or alkoxy having 1 to 4 carbon atoms or halogen atom, and R₃ represents acetyl or benzoyl group.

4. The process according to claim 1, wherein the organic carboxylic acid is aliphatic or aromatic carboxylic acid.

5. The process according to claim 4, wherein the organic carboxylic acid is selected from the group consisting of acetic acid, haloacetic acid, propionic acid, butyric acid, isobutyric acid, valeric acid, benzoic acid, halobenzoic acid and methoxybenzoic acid.

6. The process according to claim 1, wherein the organic carboxylic acid or its salt is used in the ratio of 1 to 5 equivalent weights with respect to one equivalent weight of the azetidinone derivative of formula (II).

7. The process according to claim 6, wherein the organic carboxylic acid or its salt is used in the ratio of 1 to 2 equivalent weights with respect to one equivalent weight of the azetidinone derivative of formula (II).

8. The process according to claim 1, wherein the reaction is carried out at the temperature ranging from −50° C. to boiling point of the solvent used in the reaction.

9. The process according to claim 1, wherein N-haloacylimide is used in the ratio of 1 to 2 equivalent weights with respect to one equivalent weight of the azetidinone derivative of formula (II).

10. The process according to claim 9, wherein N-haloacylimide is used in the ratio of 1 to 1.2 equivalent weights with respect to one equivalent weight of the azetidinone derivative of formula (II).

11. The process according to claim 1, wherein the reaction is carried out in the presence of a solvent.

12. The process according to claim 11, wherein the solvent is a reaction-inert organic solvent selected from the group consisting of chloroform, dichloromethane, tetrahydrofuran, dimethylformamide, acetonitrile and benzene.

13. The process according to claim 8, wherein the reaction is carried out at the temperature ranging from −20° C. to room temperature.

* * * * *